(12) United States Patent
Watson et al.

(10) Patent No.: US 9,259,188 B2
(45) Date of Patent: Feb. 16, 2016

(54) METHODS AND SYSTEMS FOR FILTERING A SIGNAL ACCORDING TO A SIGNAL MODEL AND CONTINUOUS WAVELET TRANSFORM TECHNIQUES

(75) Inventors: James Nicholas Watson, Dunfermline (GB); Paul Stanley Addison, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 744 days.

(21) Appl. No.: 13/563,675

(22) Filed: Jul. 31, 2012

(65) Prior Publication Data

US 2012/0302895 A1 Nov. 29, 2012

Related U.S. Application Data

(63) Continuation of application No. 12/245,356, filed on Oct. 3, 2008, now Pat. No. 8,235,911.

(60) Provisional application No. 61/080,842, filed on Jul. 15, 2008, provisional application No. 61/080,873, filed on Jul. 15, 2008, provisional application No. 61/081,023, filed on Jul. 15, 2008, provisional application No. 61/081,028, filed on Jul. 15, 2008.

(51) Int. Cl.
*A61B 5/00* (2006.01)
*A61B 5/1455* (2006.01)
(52) U.S. Cl.
CPC .............. *A61B 5/726* (2013.01); *A61B 5/14551* (2013.01); *A61B 5/7203* (2013.01)
(58) Field of Classification Search
CPC ....................................................... A61B 5/726
See application file for complete search history.

(56) References Cited

U.S. PATENT DOCUMENTS

| | | | |
|---|---|---|---|
| 4,289,141 | A | 9/1981 | Cormier |
| 5,439,483 | A | 8/1995 | Duong-Van |
| 5,482,036 | A | 1/1996 | Diab et al. |
| 5,490,505 | A | 2/1996 | Diab et al. |
| 5,590,650 | A | 1/1997 | Genova |
| 5,632,272 | A | 5/1997 | Diab et al. |
| 5,685,299 | A | 11/1997 | Diab et al. |
| 5,769,785 | A | 6/1998 | Diab et al. |
| 5,778,881 | A | 7/1998 | Sun et al. |

(Continued)

FOREIGN PATENT DOCUMENTS

| | | |
|---|---|---|
| JP | 09-084776 | 3/1997 |
| WO | WO 01/25802 | 4/2001 |

(Continued)

OTHER PUBLICATIONS

Mendelson, Y. Pulse oximetry: Theory and applications for noninvasive monitoring. Clinical Chemistry 38, 1601-1607 (1992).*

(Continued)

*Primary Examiner* — Soren Harward
(74) *Attorney, Agent, or Firm* — Shvarts & Leiz LLP

(57) ABSTRACT

According to embodiments, systems and methods are provided for filtering a signal. A first reference signal may be generated according to a signal model and a second reference signal may be generated by analyzing a continuous wavelet transform of a signal. The first and second reference signals may then both be applied to an input signal to filter the input signal according to the components of both of the reference signals.

14 Claims, 14 Drawing Sheets

(56) References Cited

U.S. PATENT DOCUMENTS

| | | | |
|---|---|---|---|
| 5,795,304 | A | 8/1998 | Sun et al. |
| 5,797,840 | A | 8/1998 | Akselrod |
| 5,827,195 | A | 10/1998 | Lander |
| 5,924,980 | A | 7/1999 | Coetzee |
| 5,967,995 | A | 10/1999 | Shusterman et al. |
| 6,002,952 | A | 12/1999 | Diab et al. |
| 6,036,653 | A | 3/2000 | Baba et al. |
| 6,094,592 | A | 7/2000 | Yorkey |
| 6,095,984 | A | 8/2000 | Amano et al. |
| 6,117,075 | A | 9/2000 | Barnea |
| 6,129,675 | A | 10/2000 | Jay |
| 6,135,952 | A | 10/2000 | Coetzee |
| 6,135,966 | A | 10/2000 | Ko |
| 6,171,257 | B1 | 1/2001 | Weil et al. |
| 6,171,258 | B1 | 1/2001 | Karakasoglu et al. |
| 6,206,830 | B1 | 3/2001 | Diab et al. |
| 6,208,951 | B1 | 3/2001 | Kumar et al. |
| 6,263,222 | B1 | 7/2001 | Diab et al. |
| 6,293,915 | B1 | 9/2001 | Amano et al. |
| 6,325,761 | B1 | 12/2001 | Jay |
| 6,361,501 | B1 | 3/2002 | Amano et al. |
| 6,393,311 | B1 | 5/2002 | Edgar, Jr. et al. |
| 6,501,975 | B2 | 12/2002 | Diab et al. |
| 6,561,986 | B2 | 5/2003 | Baura |
| 6,608,934 | B2 | 8/2003 | Scheirer |
| 6,654,623 | B1 | 11/2003 | Kastle |
| 6,778,923 | B2 * | 8/2004 | Norris et al. ............ 702/74 |
| 6,810,277 | B2 | 10/2004 | Edgar, Jr. et al. |
| 6,931,269 | B2 | 8/2005 | Terry |
| 6,961,742 | B2 | 11/2005 | Neretti et al. |
| 7,001,337 | B2 | 2/2006 | Dekker |
| 7,020,507 | B2 | 3/2006 | Scharf |
| 7,035,679 | B2 | 4/2006 | Addison |
| 7,043,293 | B1 | 5/2006 | Baura |
| 7,054,453 | B2 | 5/2006 | Causevic |
| 7,054,454 | B2 | 5/2006 | Causevic et al. |
| 7,079,888 | B2 | 7/2006 | Oung |
| 7,167,746 | B2 | 1/2007 | Pederson |
| 7,171,269 | B1 | 1/2007 | Addison |
| 7,173,525 | B2 | 2/2007 | Albert |
| 7,203,267 | B2 | 4/2007 | De Man et al. |
| 7,225,013 | B2 | 5/2007 | Geva et al. |
| 7,254,500 | B2 | 8/2007 | Makeig |
| 7,289,835 | B2 | 10/2007 | Mansfield |
| 7,515,949 | B2 | 4/2009 | Norris |
| 7,519,488 | B2 | 4/2009 | Fu |
| 7,523,011 | B2 | 4/2009 | Akiyama et al. |
| 2003/0163057 | A1 | 8/2003 | Flick et al. |
| 2005/0043616 | A1 | 2/2005 | Chinchoy |
| 2005/0043763 | A1 | 2/2005 | Marcovecchio et al. |
| 2005/0070774 | A1 * | 3/2005 | Addison et al. ............ 600/323 |
| 2006/0209631 | A1 | 9/2006 | Melese et al. |
| 2006/0229519 | A1 | 10/2006 | Fujiwara et al. |
| 2006/0258921 | A1 | 11/2006 | Addison et al. |
| 2006/0265022 | A1 | 11/2006 | John et al. |
| 2007/0021673 | A1 | 1/2007 | Arbel et al. |
| 2007/0066908 | A1 | 3/2007 | Graupe et al. |
| 2007/0073120 | A1 | 3/2007 | Li et al. |
| 2007/0073124 | A1 | 3/2007 | Li et al. |
| 2007/0167694 | A1 | 7/2007 | Causevic et al. |
| 2007/0167851 | A1 | 7/2007 | Vitali et al. |
| 2007/0282212 | A1 | 12/2007 | Sierra et al. |
| 2008/0045832 | A1 | 2/2008 | McGrath |
| 2008/0082018 | A1 | 4/2008 | Sackner et al. |
| 2008/0125668 | A1 | 5/2008 | Graupe et al. |
| 2008/0214903 | A1 | 9/2008 | Orbach |
| 2008/0243021 | A1 | 10/2008 | Causevic et al. |
| 2009/0076402 | A1 * | 3/2009 | Hoium ............ A61B 5/726 600/515 |
| 2009/0204162 | A1 * | 8/2009 | Addison ............ A61B 5/726 600/509 |
| 2009/0326831 | A1 * | 12/2009 | McGonigle et al. ............ 702/19 |

FOREIGN PATENT DOCUMENTS

| | | |
|---|---|---|
| WO | WO 01/62152 | 8/2001 |
| WO | WO 01/82099 | 11/2001 |
| WO | WO 03/000125 | 1/2003 |
| WO | WO 03/055395 | 7/2003 |
| WO | WO 2004/105601 | 12/2004 |
| WO | WO 2005/096170 | 10/2005 |
| WO | WO 2006/034024 A2 | 3/2006 |
| WO | WO 2006/081447 A2 | 8/2006 |
| WO | WO 2006/085120 | 8/2006 |

OTHER PUBLICATIONS

Sheng, Y. Wavelet Transform. Chapte 10 of the Transforms and Applications Handbook (Poularikas, A. D.) 1-88 (CRC Press, 2000).*

Addison, Paul S., The Illustrated Wavelet Transform Handbook, Taylor & Francis Group, 2002, pp. 1-353.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, vol. 21, No. 1, Feb. 2007, pp. 55-61.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, vol. 20, No. 1, Feb. 2006, pp. 33-36.

Leonard, Paul A., Clifton, David, Addison, Paul S., Watson, James N., Beattie, Tom, "An Automated Algorithm for Determining Respiratory Rate by Photoplethysmogram in Children," Acta Paediatricia, vol. 95, No. 9, Sep. 2006, pp. 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

Ostlund, Nils, Yu, Jun, Karlsson, Stefan, J., "Adaptive Spatio-Temporal Filtering of Multichannel Surface EMG Signals," Medical and Biological Engineering and Computing, vol. 44, (2006), pp. 209-215.

* cited by examiner

METHODS AND SYSTEMS FOR FILTERING A SIGNAL ACCORDING TO A SIGNAL MODEL AND CONTINUOUS WAVELET TRANSFORM TECHNIQUES

CROSS-REFERENCE TO RELATED APPLICATIONS

This application is a continuation of U.S. patent application Ser. No. 12/245,356 entitled "Methods and Systems for Filtering a Signal According to a Signal Model and Continuous Wavelet Transform Techniques," filed Oct. 3, 2008, which claims the benefit of U.S. Provisional Patent Application Nos. 61/080,842, entitled "Systems and Methods for Generating Reference Signals," 61/080,873, entitled "Methods and Systems for Filtering a Signal According to a Signal Model and Continuous Wavelet Transform Techniques," 61/081,023, entitled "Systems and Methods for Adaptively Filtering Signals," and 61/081,028, entitled, "Signal Processing Systems and Methods Using Multiple Signals" all filed Jul. 15, 2008, which are hereby incorporated by reference herein in their entireties.

SUMMARY

The present disclosure relates to signal processing systems and methods, and more particularly, to systems and methods for using continuous wavelet transforms to generate reference signals.

The advantages of the Continuous Wavelet Transform (CWT), including, for example, inherent resolution in both scale and time, may be used to identify and characterize features within any type of signal. The regions and amplitudes within the scalogram of the signal (or the energy density function of a wavelet transform of the signal) associated with these features may then be isolated and extracted and used (possibly using the inverse wavelet transform) to produce a reference signal for future use. This new reference signal may be especially useful for the filtering or denoising of a signal (e.g., of a concurrently collected second signal).

For example, an artifact in the original signal may be identified in the scalogram through the artifact's abnormal shape and energy density with respect to surrounding areas in the scalogram. The amplitudes associated with this feature may then be extracted and an inverse CWT may be performed to produce a reference signal indicative of the artifact. The reference signal may then be used to filter or denoise a signal using conventional techniques, such as Kalman filtering, least-mean-square (LMS) filtering, or any other suitable adaptive filtering technique. This filtering process may facilitate the determination of more accurate estimates of parameters (e.g., physiological parameters).

Additionally or alternatively, the scalogram of extracted data may be used directly with the scalogram of the signal to be filtered in order to denoise the signal in the wavelet domain. This may have added advantages due to the filtering being applied in the time-scale space rather than the spectral or time domain.

In some embodiments, these signal processing techniques may be combined with signal models to derive a more accurate reference signal for the filtering of signals containing noise. For example, where a suitable relationship is assumed between signal and noise between two signal portions or between two signals (e.g., two photoplethysmograph (PPG) signals in the case of pulse oximetry) then a reference signal may be derived from one or more suitable signal models. This reference signal may be combined, for example, additively, with a reference signal from, for example, a wavelet processor implementing a continuous wavelet transform to provide a more effective reference signal. An input signal may then be filtered using at least the reference signal derived from the signal model and the reference signal derived from the continuous wavelet transform.

Alternatively, adaptive filtering, such as Kalman or LMS filtering, may be employed to filter the signal prior to its input to a wavelet filter where further filtering (e.g., of temporal artifacts such as spikes) may be carried out. The complementary strength of the two filter components (e.g., a non-wavelet and wavelet filter component) may provide superior results over applying either filter component in isolation.

In some embodiments, a first signal and a second signal are received, for example, by a sensor or probe. At least two scalograms may then be generated based at least in part on the received first signal, the received second signal, or both received signals. At least one of these generated scalograms may be a residual scalogram created by subtracting components of one scalogram from corresponding components of another scalogram. One or both of the scalograms may be multiplied by some scaling factor prior to the subtraction. A scalogram mask may then be generated from the residual scalogram. For example, in some embodiments, regions of the residual scalogram that do not exceed some predefined threshold value may form at least part of the areas to be masked. The scalogram mask may then be applied to one of the first and second scalograms in order to generate a modified or masked scalogram. From this modified or masked scalogram, more reliable and accurate parameters (e.g., physiological parameters) may be determined.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 3(*c*) shows an illustrative schematic of a wavelet transform of a signal containing two pertinent components in accordance with an embodiment;

FIG. 3(*d*) shows an illustrative schematic of signals associated with a ridge in FIG. 3(*c*) and schematics of a further wavelet decomposition of these newly derived signals in accordance with an embodiment;

FIGS. 3(*e*) and 3(*f*) show flow charts of illustrative steps involved in performing an inverse continuous wavelet transform in accordance with embodiments;

DETAILED DESCRIPTION

Figure 1:
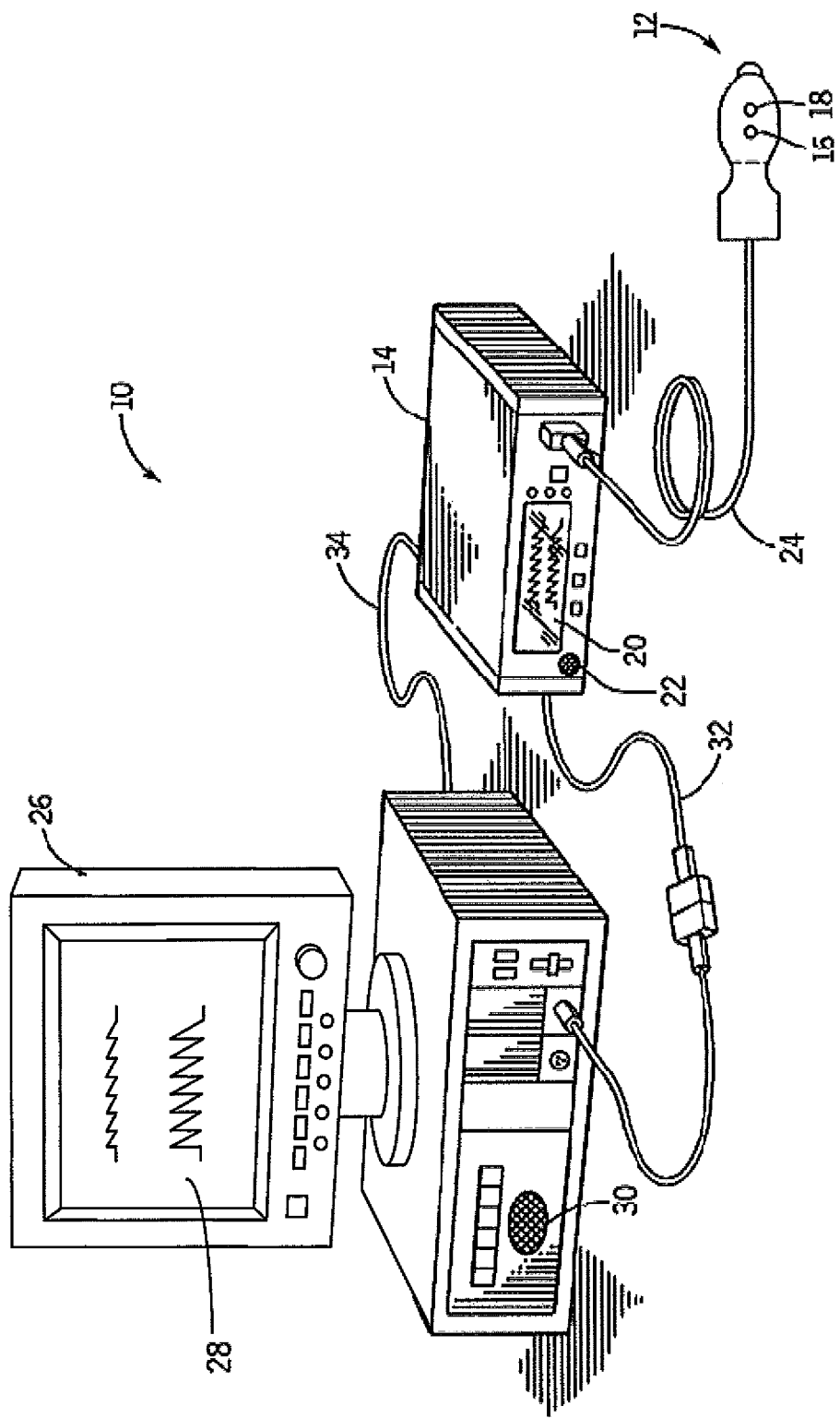
FIG. 1 is a perspective view of a pulse oximetry system.

In medicine, a plethysmograph is an instrument that measures physiological parameters, such as variations in the size of an organ or body part, through an analysis of the blood passing through or present in the targeted body part, or a depiction of these variations. An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{\frac{dI}{dt}}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

The optical signal through the tissue can be degraded by noise, among other sources. One source of noise is ambient light which reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, since blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

FIG. 1 is a perspective view of an embodiment of a pulse oximetry system 10. The system 10 includes a sensor 12 and a pulse oximetry monitor 14. The sensor 12 includes an emitter 16 for emitting light at two or more wavelengths into a patient's tissue. A detector 18 is also provided in the sensor 12 for detecting the light originally from the emitter 16 that emanates from the patient's tissue after passing through the tissue.

According to another embodiment and as will be described, the system 10 may include a plurality of sensors forming a sensor array in lieu of the single sensor 12. Each of the sensors of the sensor array may be a complementary metal oxide semiconductor (CMOS) sensor. Alternatively, each sensor of the array may be charged coupled device (CCD) sensor. In yet another embodiment, the sensor array may be made up of a combination of CMOS and CCD sensors. The CCD sensor comprises a photoactive region and a transmission region for receiving and transmitting data while the CMOS sensor is made up of an integrated circuit having an array of pixel sensors. Each pixel has a photodetector and an active amplifier.

According to an embodiment, the emitter 16 and detector 18 may be on opposite sides of a digit such as a finger or toe, in which case the light that is emanating from the tissue has passed completely through the digit. In an embodiment, the emitter 16 and detector 18 may be arranged so that light from the emitter 16 penetrates the tissue and is reflected by the tissue into the detector 18, such as a sensor designed to obtain pulse oximetry data from a patient's forehead.

In an embodiment, the sensor or sensor array may be connected to and draw its power from the monitor 14 as shown. In another embodiment, the sensor may be wirelessly connected to the monitor 14 and include its own battery or similar power supply (not shown). The monitor 14 may be configured to calculate physiological parameters based on data received from the sensor 12 relating to light emission and detection. In an alternative embodiment, the calculations may be performed on the monitoring device itself and the result of the oximetry reading is simply passed to the monitor 14. Further, the monitor 14 includes a display 20 configured to display the physiological parameters or other information about the system. In the embodiment shown, the monitor 14 also includes a speaker 22 to provide an audible sound that may be used in various other embodiments, such as for example, sounding an alarm in the event that a patient's physiological parameters are not within a predefined normal range.

In an embodiment, the sensor 12, or the sensor array, is communicatively coupled to the monitor 14 via a cable 24. However, in other embodiments a wireless transmission device (not shown) or the like may be utilized instead of or in addition to the cable 24.

In the illustrated embodiment, the pulse oximetry system 10 also includes a multi-parameter patient monitor 26. The monitor may be cathode ray tube type, a flat panel display (as shown) such as a liquid crystal display (LCD) or a plasma display, or any other type of monitor now known or later developed. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display an estimate of a patient's blood oxygen saturation generated by the pulse oximetry monitor 14 (referred to as an "SpO$_2$" measurement), pulse rate information from the monitor 14 and blood pressure from a blood pressure monitor (not shown) on the display 28.

The monitor 14 may be communicatively coupled to the multi-parameter patient monitor 26 via a cable 32 or 34 coupled to a sensor input port or a digital communications port, respectively and/or may communicate wirelessly (not shown). In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

Figure 2:
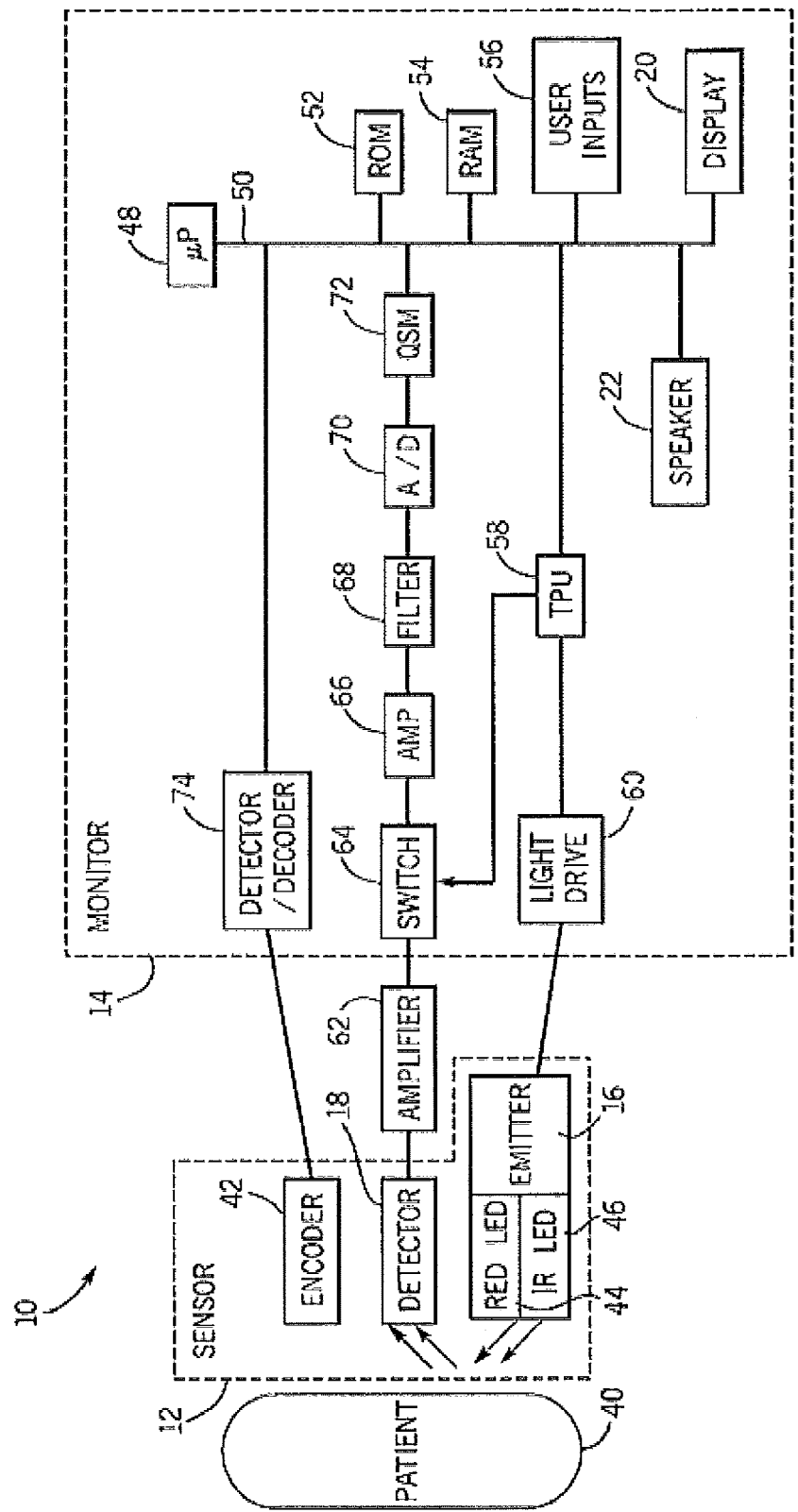
FIG. 2 is a block diagram of the exemplary pulse oximetry system of FIG. 1 coupled to a patient.

FIG. 2 is a block diagram of the embodiment of a pulse oximetry system 10 of FIG. 1 coupled to a patient 40 in accordance with present embodiments. Specifically, certain components of the sensor 12 and the monitor 14 are illustrated in FIG. 2. The sensor 12 includes the emitter 16, the detector 18, and an encoder 42. In the embodiment shown, the emitter 16 is configured to emit at least two wavelengths of light, e.g., RED and IR, into a patient's tissue 40. Hence, the emitter 16 may include a RED light emitting light source such as the RED light emitting diode (LED) 44 shown and an IR light emitting light source such as the IR LED 46 shown for emitting light into the patient's tissue 40 at the wavelengths used to calculate the patient's physiological parameters. In certain embodiments, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It should be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein light may also include any wavelength within the radio, microwave, infrared, visible, ultraviolet, or X-ray spectra, and that any suitable wavelength of electromagnetic radiation may be appropriate for use with the present techniques. Similarly, detector 18 may be chosen to be specifically sensitive to the chosen targeted energy spectrum of the emitter 16.

In an embodiment, the detector 18 may be configured to detect the intensity of light at the RED and IR wavelengths. Alternatively, each sensor in the array may be configured to detect an intensity of a single wavelength. In operation, light enters the detector 18 after passing through the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40.

In an embodiment, the encoder 42 may contain information about the sensor 12, such as what type of sensor it is (e.g., whether the sensor is intended for placement on a forehead or digit) and the wavelengths of light emitted by the emitter 16. This information may be used by the monitor 14 to select appropriate algorithms, lookup tables and/or calibration coefficients stored in the monitor 14 for calculating the patient's physiological parameters.

In addition, the encoder 42 may contain information specific to the patient 40, such as, for example, the patient's age, weight, and diagnosis. This information may allow the monitor 14 to determine patient-specific threshold ranges in which the patient's physiological parameter measurements should fall and to enable or disable additional physiological parameter algorithms. The encoder 42 may, for instance, be a coded resistor which stores values corresponding to the type of the sensor 12 or the type of each sensor in the sensor array, the wavelengths of light emitted by the emitter 16 on each sensor of the sensor array, and/or the patient's characteristics. In another embodiment, the encoder 42 may include a memory on which one or more of the following information may be stored for communication to the monitor 14: the type of the sensor 12; the wavelengths of light emitted by the emitter 16; the particular wavelength each sensor in the sensor array is monitoring; and a signal threshold for each sensor in the sensor array.

In an embodiment, signals from the detector 18 and the encoder 42 may be transmitted to the monitor 14. In the embodiment shown, the monitor 14 includes a general-purpose microprocessor 48 connected to an internal bus 50. The microprocessor 48 is adapted to execute software, which may include an operating system and one or more applications, as part of performing the functions described herein. Also connected to the bus 50 are a read-only memory (ROM) 52, a random access memory (RAM) 54, user inputs 56, the display 20, and the speaker 22.

The RAM 54 and ROM 52 are illustrated by way of example, and not limitation. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 provides timing control signals to a light drive circuitry 60 which controls when the emitter 16 is illuminated and multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the A/D converter 70 for multiple light wavelengths or spectra received.

In an embodiment, the microprocessor 48 may determine the patient's physiological parameters, such as $SpO_2$ and pulse rate, using various algorithms and/or look-up tables based on the value of the received signals and/or data corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52. The user inputs 56 may be used to enter information about the patient, such as age, weight, height, diagnosis, medications, treatments, and so forth. In certain embodiments, the display 20 may exhibit a list of values which may generally apply to the patient, such as, for example, age ranges or medication families, which the user may select using the user inputs 56.

The embodiments described herein may relate to determining one or more statistical parameters of data from which an estimated physiological parameter value has been determined. Statistical parameters associated with the physiological parameter may include parameters related to the accuracy of the estimated value such as error estimates and probability distributions of the data.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right)dt \qquad (9)$$

where $\psi^*(t)$ is the complex conjugate of the wavelet function $\psi(t)$, a is the dilation parameter of the wavelet and b is the location parameter of the wavelet. The transform given by equation (9) can be used to construct a representation of a signal on a transform surface. The transform may be regarded as a time-scale representation. Wavelets are composed of a range of frequencies, one of which may be denoted the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found in the general literature.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain. As a further example, to reconstruct a temporal signal requires integrating twice, across time and scale, in the wavelet domain while, conversely, one integration across frequency is required to derive a temporal signal from a spectral domain). It is well known in the art that, as well as amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '|| ' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required $\alpha$ scale and then multiplying the result by $\sqrt{\alpha}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
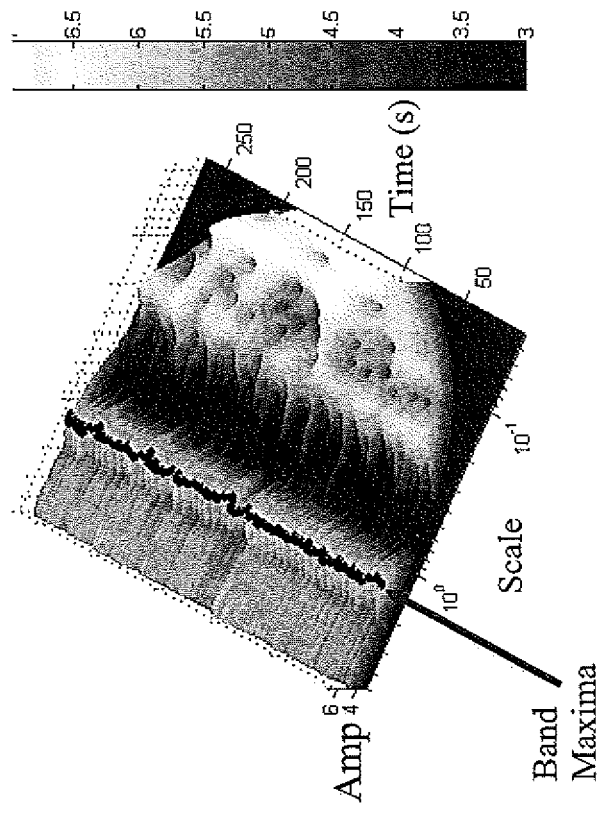
FIGS. 3(*a*) and 3(*b*) show illustrative views of a scalogram derived from a PPG signal in accordance with an embodiment.
Figure 3A:
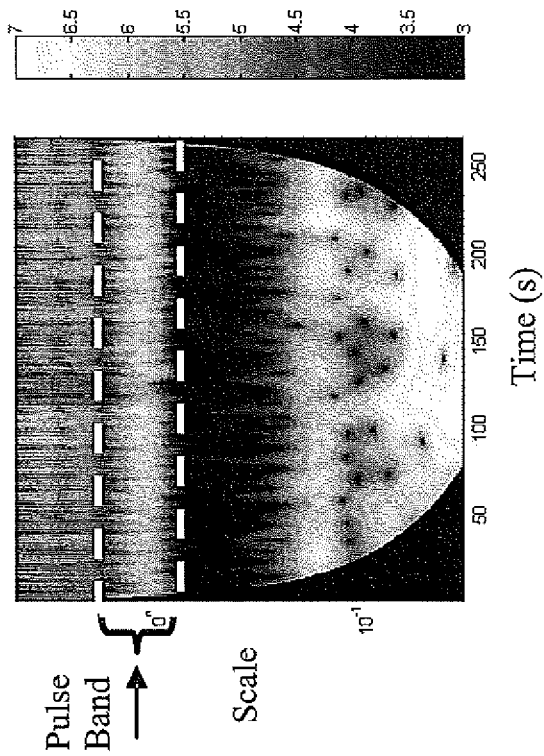

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) contain two views of a scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
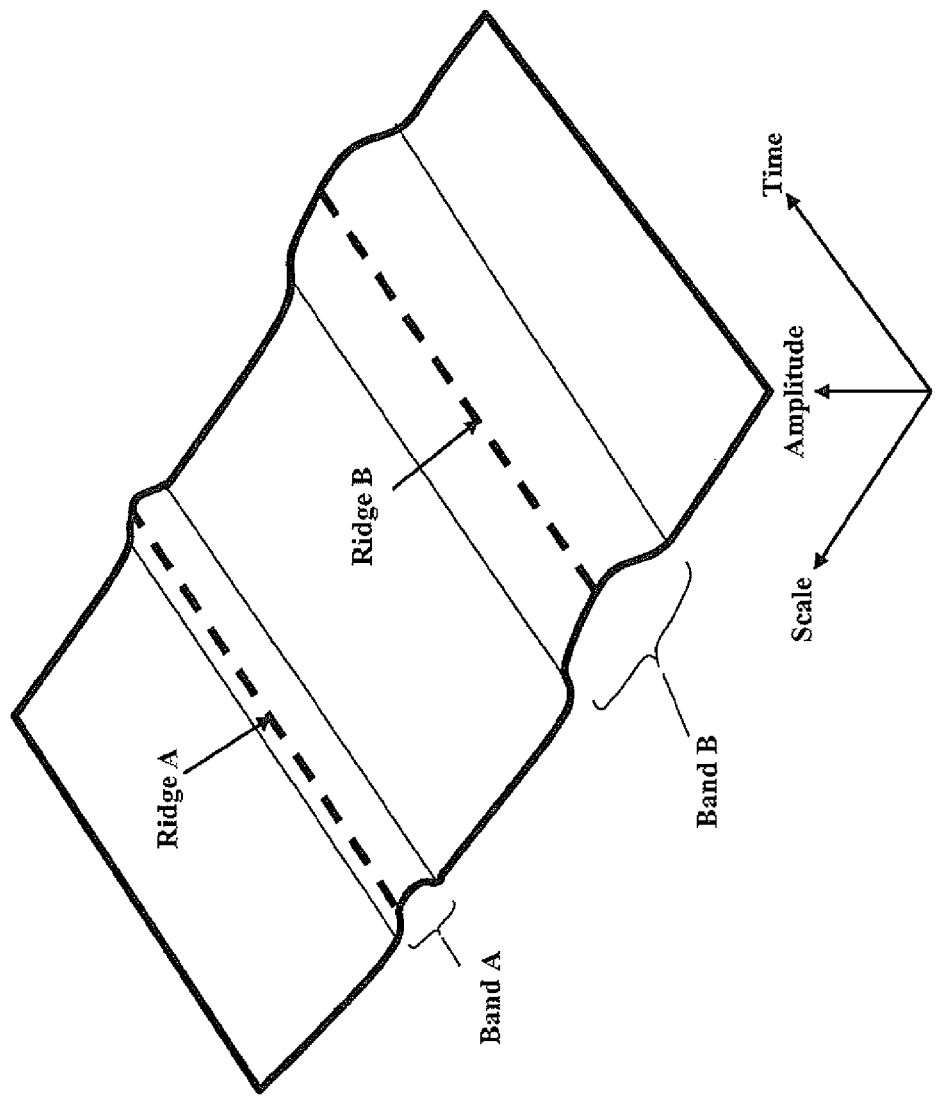
Figure 3D:
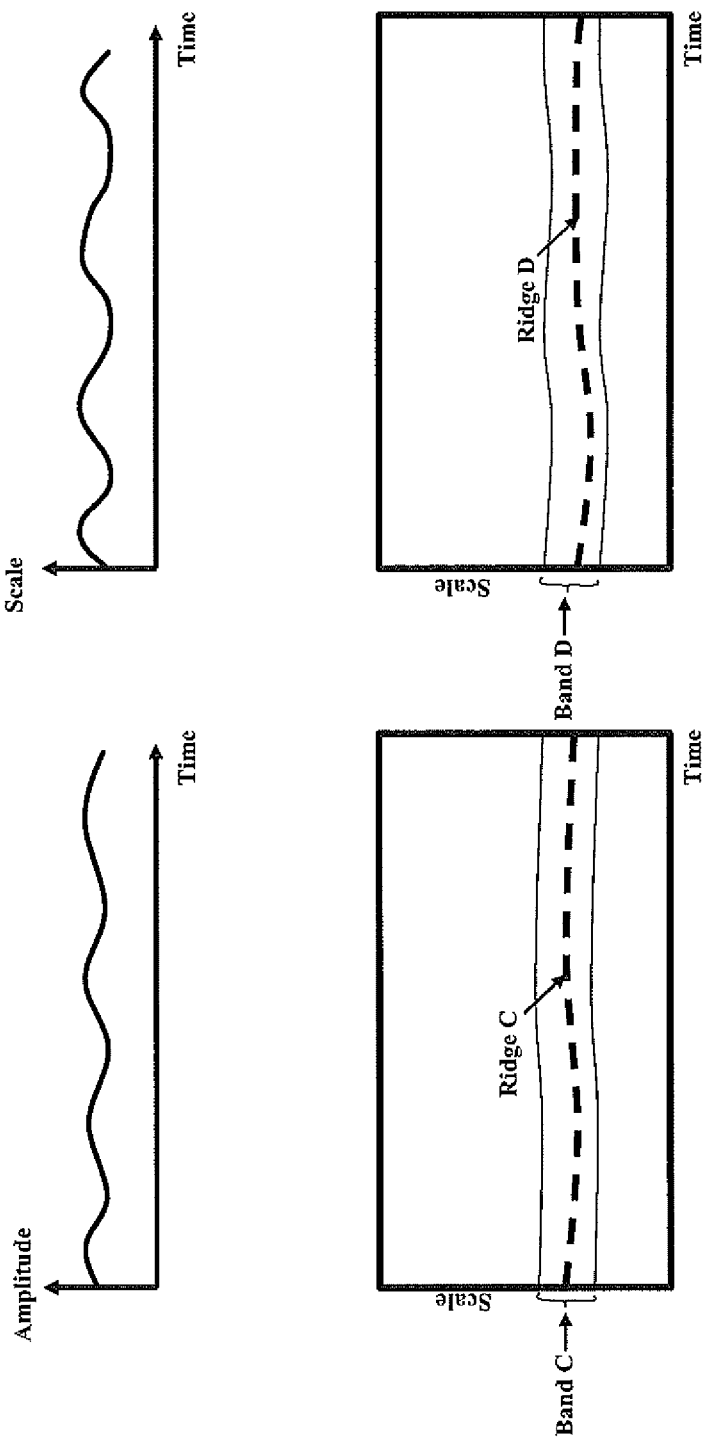

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\,db}{a^2} \quad (a)$$

which may also be written as:

$$x(t) = \frac{1}{C_g} \int_{-\infty}^{\infty} \int_{0}^{\infty} T(a,b) \psi_{a,b}(t) \frac{da\,db}{a^2} \quad (b)$$

where $C_g$ is a scalar value known as the admissibility constant. It is wavelet type dependent and may be calculated from:

$$C_g = \int_{0}^{\infty} \frac{|\hat{\psi}(f)|^2}{f} df \quad (c)$$

Figure 3E:
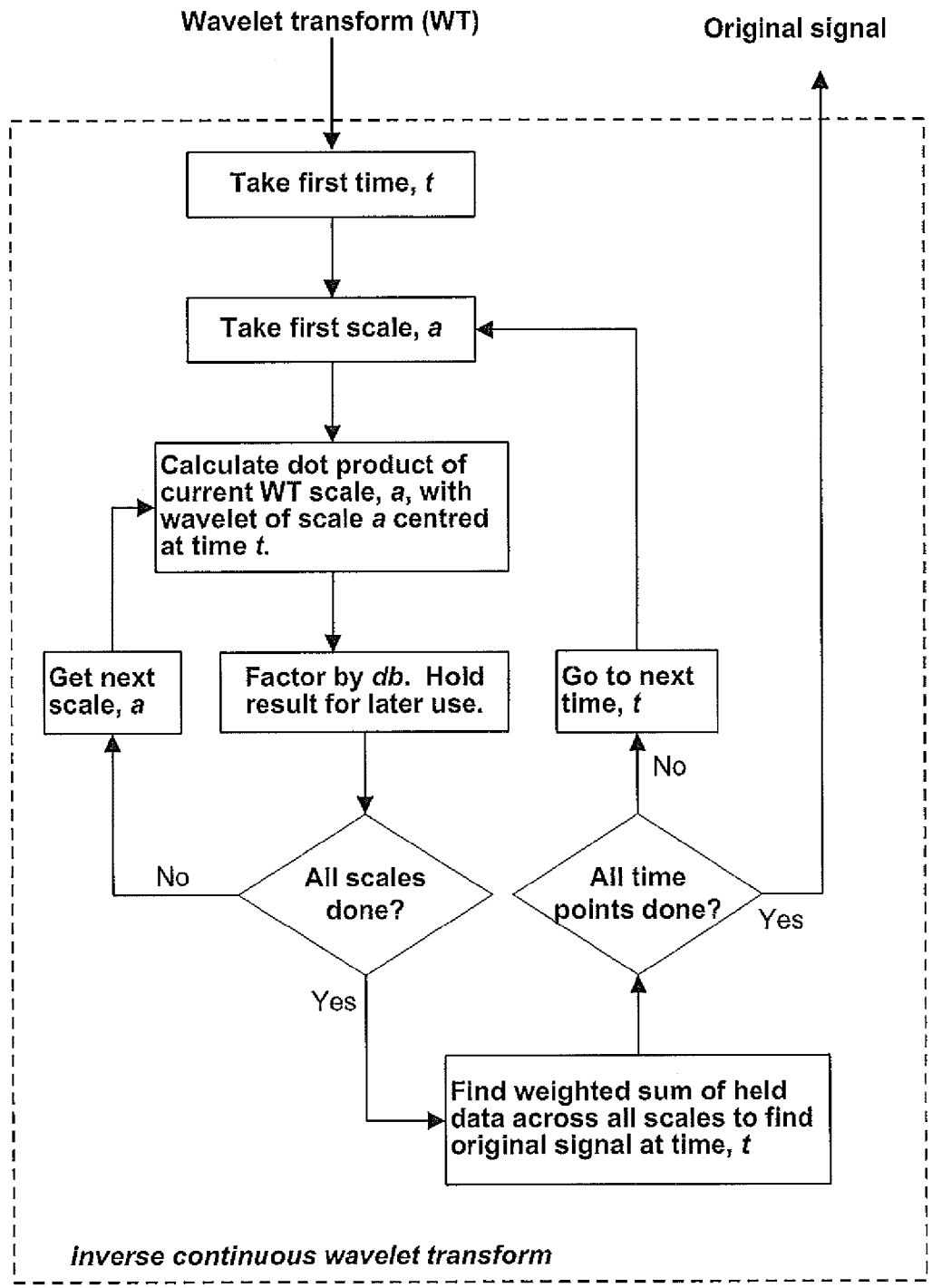
Figure 3F:
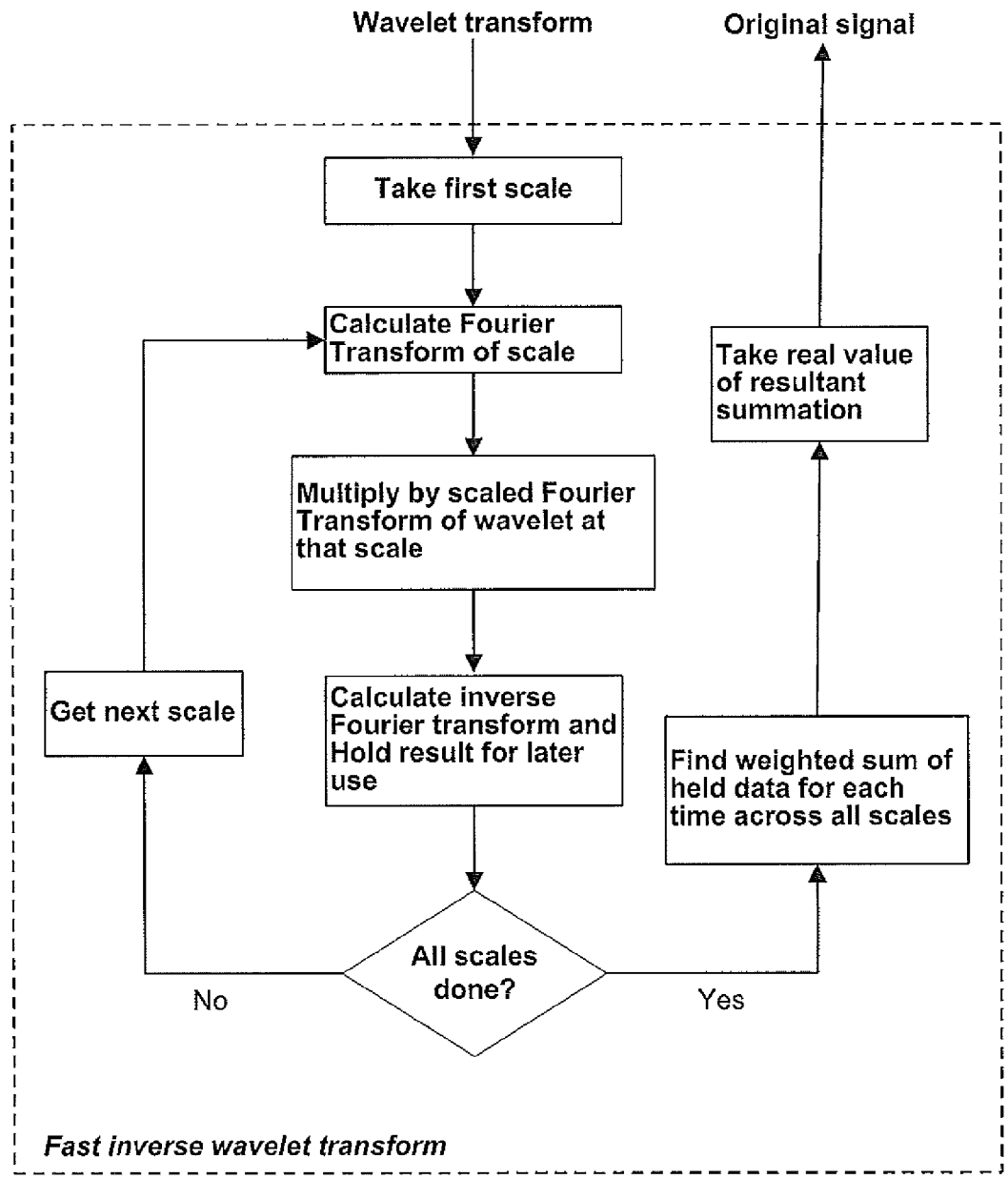

FIG. 3(e) is a flow chart of illustrative steps that may be taken to perform an inverse continuous wavelet transform in accordance with the above discussion. An approximation to the inverse transform may be made by considering equation (a) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform.

Figure 4:
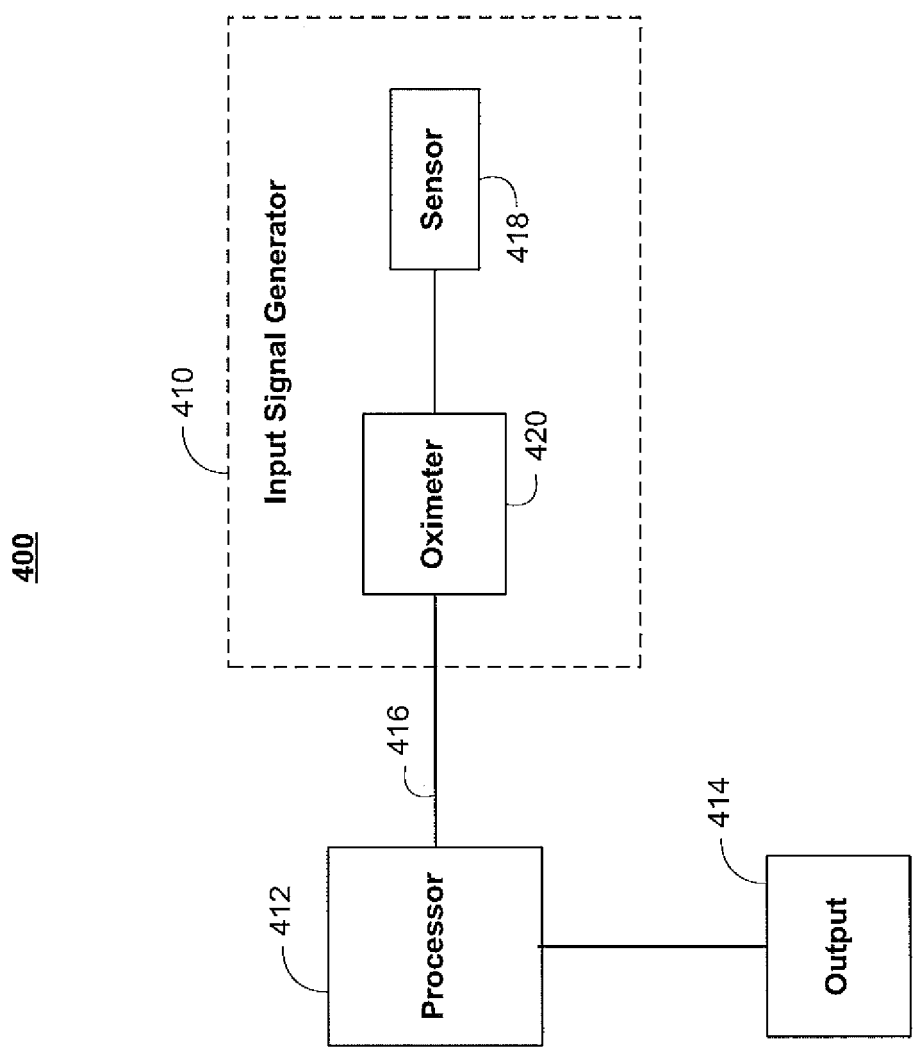
FIG. 4 shows an illustrative continuous wavelet processing system in accordance with an embodiment.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In an embodiment, physiological parameters may be calculated from signals. For example, pulse rate or respiration rate may be calculated from a red or infrared PPG signal by first taking a continuous wavelet transform of the PPG signal. A scalogram may then be derived from the wavelet transform. The scalogram may be generated as discussed above. For real wavelet transforms, the transform itself may be used as the scalogram. Alternatively, the real or imaginary part of a complex wavelet may be used as the scalogram. A physiological parameter may be determined from the scalogram by analyzing features on the scalogram. For example, the location of ridges on the scalogram may be used to calculate pulse rate or respiration rate. In an embodiment, a secondary wavelet transform may be taken of the RAP and/or RSP signals derived from the pulse band to calculate respiration rate. Techniques for calculating parameters such as respiration rate are described in Addison et al. U.S. Pat. No. 7,035,679, issued Apr. 25, 2006, and Addison et al. U.S. Patent Publication No. 2006/0258921, published Nov. 16, 2006, both of which are incorporated by reference herein in their entireties.

Oxygen saturation may also be calculated from PPG signals (e.g., using red and infrared PPG signals). Techniques for calculating oxygen saturation using wavelet transforms are also described in Addison et al. U.S. Pat. No. 7,035,679.

Accordingly, one PPG signal may be used to calculate pulse rate and respiration rate and two PPG signals may be used to calculate oxygen saturation. Improved parameter calculations may be implemented by using additional signals. For example, an improved pulse rate and respiration rate may be calculated using information from multiple PPG signals. In addition, an improved oxygen saturation may be calculated using more than two PPG signals.

Figure 5:
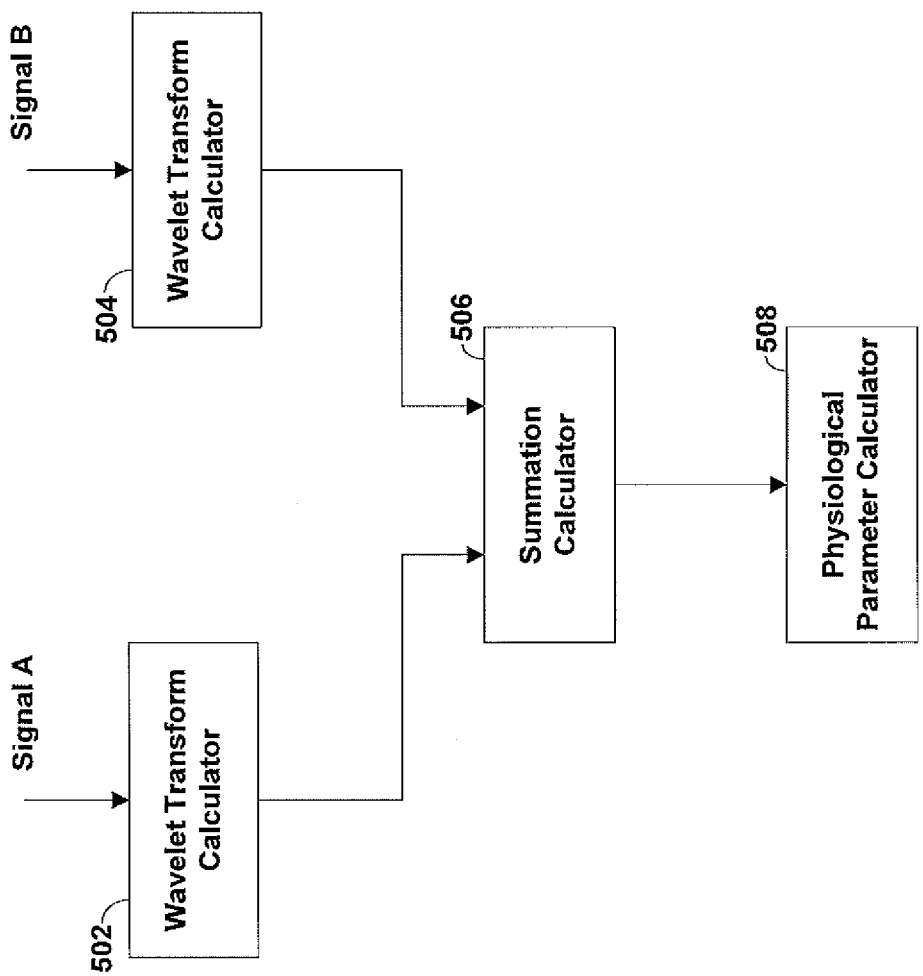
FIG. 5 shows a functional block diagram of a signal processor that uses multiple signals to calculate a desired parameter.

FIG. 5 shows a functional block diagram of a signal processor that uses multiple signals to calculate a desired parameter. Signal A may be received at wavelet transform calculator 502 and Signal B may be received at wavelet transform calculator 504. In an embodiment, signal A may be a red PPG signal and signal B may be an infrared PPG signal. In another embodiment, signal A may be a red PPG signal (or infrared PPG signal) and signal B may be another red PPG signal (or infrared PPG signal) taken at a different location. Wavelet transform calculators 502 and 504 may perform similar or different wavelet transforms of the received signals. For example, wavelet transform calculators 502 and 504 may perform continuous wavelet transforms of signals A and B, respectively, using complex wavelets. In an embodiment, wavelet transform calculator 502 may use one type of wavelet and wavelet transform calculator 504 may use a wavelet having identical characteristics or differing characteristics (e.g., differing in oscillations or characteristic frequency). Wavelet transform calculators 502 and 504 may output wavelet transforms or scalograms derived therefrom to summation calculator 506. For clarity, the remaining elements of the functional block diagram of FIG. 5 will be discussed as processing scalograms. It will be understood that the same or similar operations may be performed on wavelet transforms.

Summation calculator 506 may combine the received scalograms to generate a modified scalogram. Summation calculator 506 may combine the received scalograms by summing the coefficients at each scale and time to generate the modified scalogram. In an embodiment, summation calculator 506 may multiply one or both scalograms by scaling factors before combining them. This may be performed to account for differences in the signals. For example, one signal may be determined to be noisier than the other signal. In such a situation, a smaller scaling factor may be applied to the noisier signal or a higher scaling factor may be applied to the less noisy signal. In another example, one of the received signals may have smaller signal components. Therefore, scaling factors may be used to normalize the two scalograms before the scalograms are combined. Summation calculator 506 may output a modified wavelet scalogram to physiological parameter calculator 508.

Physiological parameter calculator 508 may calculate a physiological parameter based at least in part on the received modified scalogram. For example, physiological parameter calculator 508 may calculate the pulse rate or respiration rate by using ridge following techniques on the modified scalogram. As another example, physiological parameter calculator 508 may calculate the respiration rate by taking a secondary wavelet transform of features in the modified scalogram.

The functional block diagram of FIG. 5 is merely illustrative and any suitable changes may be made in accordance with the present disclosure. For example, two additional wavelet transform calculators and one additional summation calculator may be used to process two additional signals to generate a second modified wavelet transform or scalogram. Physiological parameter calculator 508 may receive the second modified scalogram. In such an arrangement, physiological parameter calculator 508 may use the two received scalograms to calculate oxygen saturation using any suitable method. The received signals in this embodiment may be red and infrared PPG signals detected at one or more locations.

In an embodiment, summation calculator 506 may be configured to subtract one received scalogram from the other received scalogram. Summation calculator 506 may subtract all or parts of one scalogram from the other scalogram. In an embodiment, summation calculator 506 may multiply one or both scalograms by scaling factors before subtracting them. This may be performed to account for differences in the signals. For example, scaling factors may be used to normalize the two scalograms before the scalograms are subtracted. For example, the scaling factors may be calculated from the ratio of amplitudes or energies in the pulse bands of the two scalograms to compensate for different signal strengths. One scalogram may then be subtracted from the other to provide a scalogram of residual values which may characterize the noise of the system. Alternatively, a series of different scaling factors may be applied to one of the scalograms. Each of these scaled scalograms may then be subtracted from the second scalogram to produce a set of residual scalograms. These residual scalograms may contain information indicative of the scaling factor necessary to normalize the noise in the scalograms and the scaling factor necessary to optimally account for differences in the signal strength (such as differences in absorption or transmittance of light of different wavelengths).

In an embodiment, summation calculator 506 may output a modified scalogram that may be representative of noise or artifact components in signal A or signal B, or noise or artifact components that are present in both signals A and B. This modified scalogram may be used to modify (e.g., divide, multiply, or subtract from) either or both of the scalograms generated by wavelet transform calculators 502 and 504 to generate second modified scalograms. The second modified scalograms may be further processed to derive physiological parameters as discussed above. In an embodiment, an inverse wavelet transform may be taken of the modified scalogram and subtracted from either or both of signals A and B to generate modified signals. The modified signals may then be processed to derive physiological parameters as discussed above. The modified signals or scalograms may also be used in connection with known adaptive filtering techniques.

In one embodiment, the modified scalogram may be representative of desired components in signal A or signal B, or desired components present in both signals A and B. The modified scalogram may then be analyzed to derive physiological parameters as discussed above.

Figure 6:
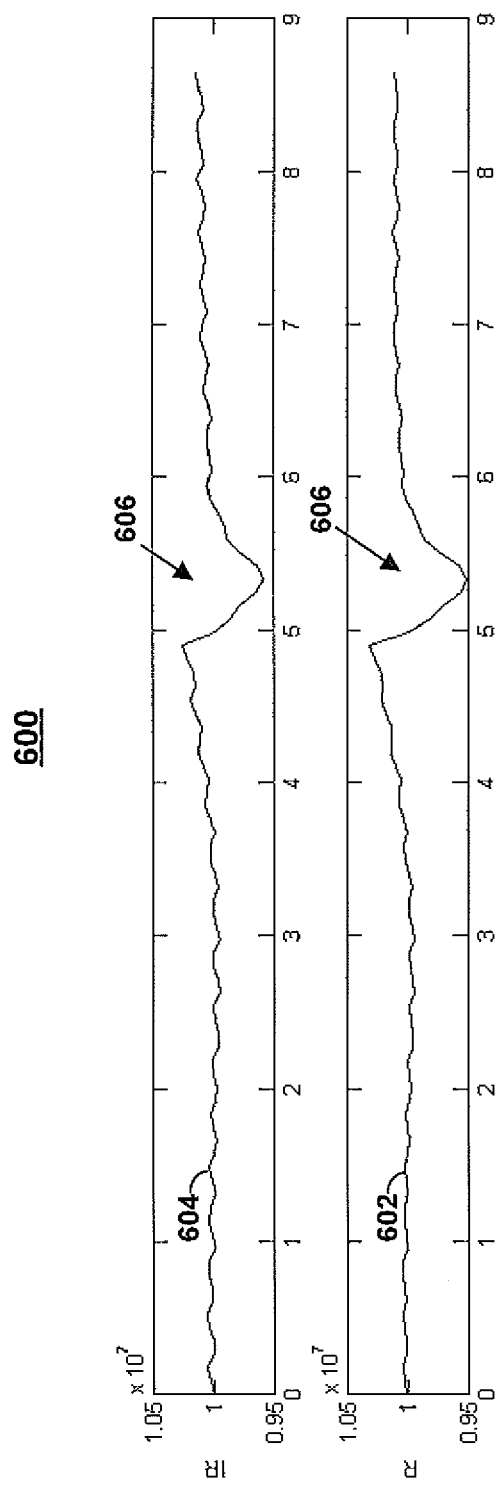
FIG. 6 shows illustrative red and infra red signal segments with an artifact in the form of a rapid baseline shift.
Figure 7A:
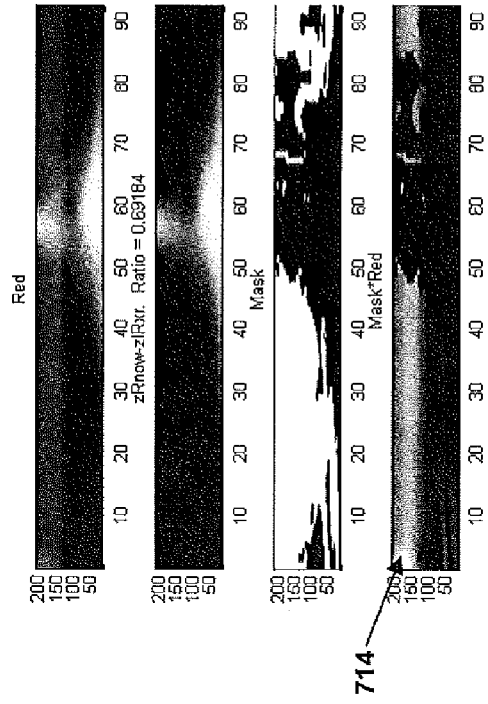
FIGS. 7A, 7B, 7C, and 7D show illustrative scalograms useful in the signal processing techniques described in the present disclosure.

FIGS. 6, 7A, 7B, 7C, 7D, and 8 illustrate an embodiment of the signal processing techniques of the present disclosure. FIG. 6 shows plots 600, including red PPG signal segment 602 and infrared PPG signal segment 604 (e.g., as obtained from a pulse oximeter) with an artifact in the form of rapid baseline shift 606 just after the half-way point of each signal. In FIG. 7A, plot 702 is a scalogram ("Red-Scalogram") generated from a portion of red signal segment 602 of FIG. 6. Red-Scalogram shows the manifestation of pulse band 706 and artifact 704 in wavelet space.

Plot 708 of FIG. 7A shows the residual scalogram ("Residual-Scalogram") obtained by subtracting from the components of the Red-Scalogram the corresponding components of a scalogram generated from a portion of infrared signal segment 604 of FIG. 6 ("IR-Scalogram") multiplied by a scaling factor of 0.3. As described in more detail below, any other suitable scaling factor may be used in other embodiments.

Plot 710 of FIG. 7A shows a time-scale mask ("TS-Mask") derived by setting those scalogram components of the Residual-Scalogram above a predefined threshold value to zero (shown black in plot 710) and the components below the predefined threshold value to one (shown white in plot 710). The predefined threshold value may be any suitable value depending on, for example, the nature of the input signals and the nature of the signal processing or filtering desired. In one embodiment, the threshold value may remain static for the length of the signal or scalogram segment to be processed. In one embodiment, the threshold value may be adjusted dynamically via a calibration sequence for improved results. For example, in one embodiment, the threshold value may be dynamically adjusted during periods of increased or decreased artifact noise. The threshold value may also be based on some percentile of a running average energy level of the scalogram (e.g., the 50th percentile) in one embodiment.

TS-Mask may then be used as a reference signal (or be used to generate a reference signal) in conjunction with adaptive filtering techniques. For example, the inverse CWT may be performed on TS-Mask to produce a reference signal indicative of an artifact. This reference signal may be used to filter or denoise a signal using conventional techniques, such as Kalman filtering, least-mean-square (LMS) filtering, or any other suitable adaptive filtering technique. Physiological parameters may then be derived more reliably from the filtered signals.

In an embodiment, the TS-Mask may additionally or alternatively be used to select pertinent Red-Scalogram components for summation. In an embodiment, this selection may be performed by selecting for summation only those Red-Scalogram components with corresponding TS-Mask components equal to one, while ignoring those Red-Scalogram components with corresponding TS-Mask components equal to zero. This is illustrated in plot 712 of FIG. 7A where the masked Red-Scalogram ("M-Red-Scalogram") is shown. The masked regions of the Red-Scalogram are shown black in plot 712.

The summation of the M-Red-Scalogram may then be plotted against the scaling factor used to generate the residual scalogram (e.g., 0.3) as a component in a Time-Scale Metric (TSM) plot. An illustrative TSM plot is shown in plot 800 of FIG. 8.

Figure 7B:
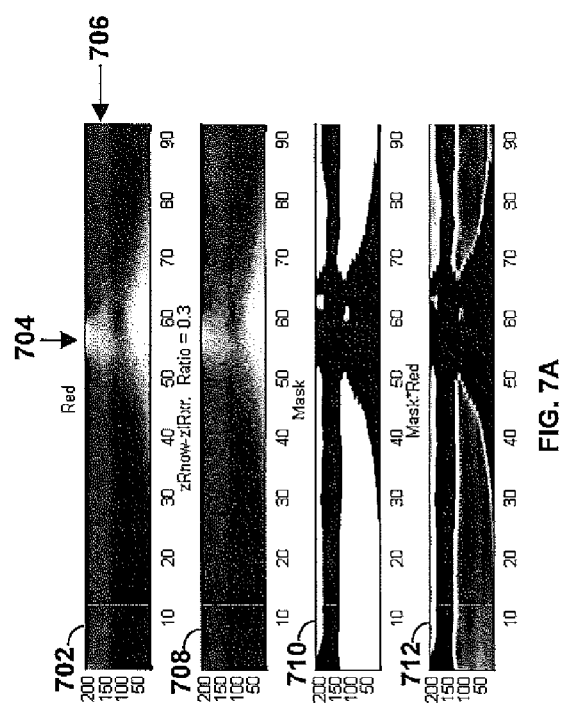
Figure 7C:
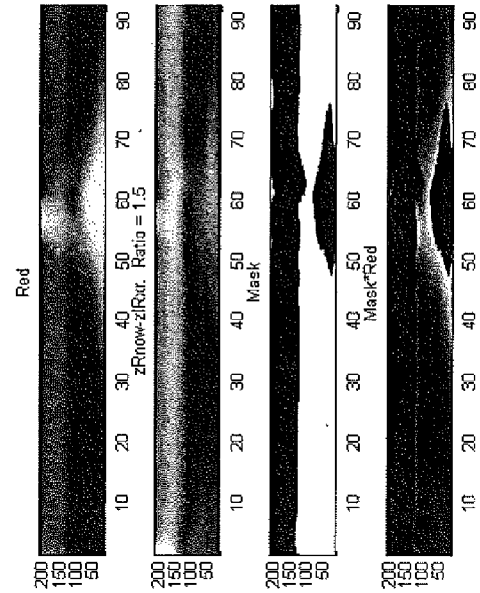
Figure 7D:
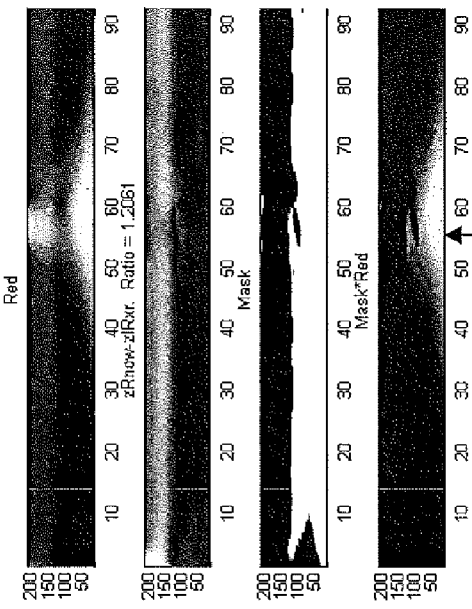

The aforementioned process may then be repeated for one or more other scaling factors, and a TSM plot may be generated across a range or plurality of these scaling factors (or some subset of these scaling factors). For example, FIGS. 7B, 7C, and 7D show the corresponding plots of FIG. 7A for scaling factors of 0.7, 1.2, and 1.5, respectively. FIG. 7B may correspond to a scaling factor near the ratio of the signal components required for accurate calculation of $SpO_2$ (approximately 0.7). As shown in the bottom plot of FIG. 7B, application of the TS-Mask may remove the artifact, leaving pulse band component 706 mainly intact. This may produce first localized peak 802 in TSM plot 800 of FIG. 8.

FIG. 7C shows a mask which may remove the pulse band but retain artifact 708 corresponding to a ratio more indicative of the artifact scaling between the two signals. For very low scaling factors (e.g., the scaling factor used in FIG. 7A) and very high scaling factors (e.g., the scaling factor used in FIG. 7D), the mask may obscure one or both of the pulse band and artifact components resulting in low values in TSM plot 800 of FIG. 8.

Figure 8:
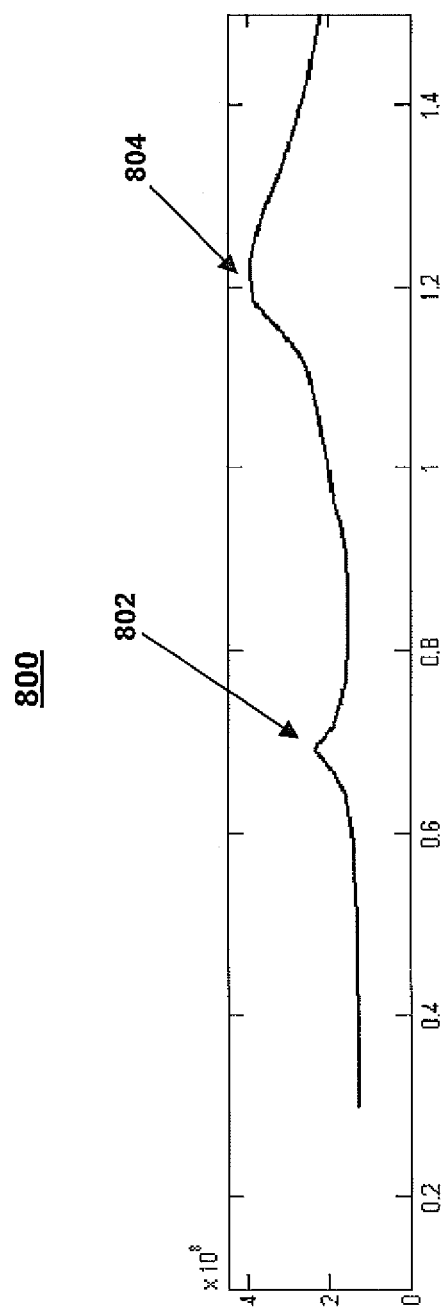
FIG. 8 shows an illustrative Time-Scale Metric (TSM) plot with two peaks.

In TSM plot 800 of FIG. 8, peak 802 occurring at a scaling factor of around 0.69 may correspond well with the known scaling factor for the signals shown in FIG. 6. The second peak, at a scaling factor of around 1.2, may correspond with the anticipated value for venous oxygen saturation as might be expected for signal components resulting from noise of the type shown in FIG. 6. TSM plot 800 of FIG. 8 may then be used to obtain information indicative of the scaling factor necessary to optimally account for differences in the signal strength (such as, in the pulse oximetry context, the differences due to the absorption or transmittance of light at different wavelengths or the different locations used to detect the signals). These scaling factors may then be used to filter or denoise a signal using conventional filtering techniques, such as Kalman filtering, LMS filtering, or advanced adaptive wavelet filtering in the time-scale plane.

Those skilled in the art will recognize that the signal processing techniques described herein have several implementation variations, including performing the inverse wavelet transform of the M-Red-Scalogram before summing the signal components, summing the power of the signal components, or summing some other useful measure. In an embodiment, the TS-Mask may be used to filter out components in other wavelet representations such as the real, imaginary, or complex components of the transform prior to performing the inverse wavelet transform.

In one embodiment, the TS-Mask may be used with the infrared scalogram (IR-Scalogram) to produce a masked IR-Scalogram from which a summation is made and plotted. A combination of summations from both the masked Red-Scalogram and masked IR-Scalogram may also be used in an embodiment.

In the example described above and illustrated in FIGS. 6, 7A, 7B, 7C, 7D, and 8, the threshold value used to create the TS-Mask may be set at the 50th percentile of the energy values in the Residual-Scalogram. As mentioned above, however, there are a number of other ways to set the threshold value used to generate the TS-Mask. For example, the threshold value may be set at another percentile of all values in the Residual-Scalogram; set as a proportion of the maximum value in the Residual-Scalogram; based, at least in part, on knowledge of the energy in various components (such as the pulse band or noise artifact features) in the original Red-Scalogram or infrared scalogram (IR-Scalogram); based, at least in part, on the comparison of each component in the Residual-Scalogram with their corresponding values in the original Red-Scalogram, IR-Scalogram, or both; or set as any other suitable threshold or any combination thereof.

The techniques described above can be applied to a subsequent portion of the signal, for example, a new portion of signal displaced by a set time period (e.g., every second, every heart beat, or any other arbitrary time period). In this way, the $SpO_2$ value may be determined from red and infrared PPG signals within a medical device that outputs continuously. The signal processing techniques described above in the time-scale plane may yield a significant improvement on techniques developed for use in either the time domain or frequency domain.

Signals, such as PPG signals, typically contain noise or artifacts (collectively referred to herein as "noise") due to any of a multitude of sources such as environmental factors, motion-induced noise, interference from equipment, cables, etc. One technique for reducing the noise present in signals involves making an assumption that there is a mathematical relationship between two measured signals $S_1$ and $S_2$. One or both of the two measured signals may be the same or similar type as the signal to be filtered (e.g., PPG signals). For example, if each of signals $S_1$ and $S_2$ contain two signal portions s (e.g., a signal portion) and n (e.g., a noise portion), whereby $S_1=s_1+n_1$ and $S_2=s_2+n_2$, then one suitable relationship between signals $S_1$ and $S_2$ may be $s_1=a*s_2$ and $n_1=b*n_2$. A value for a and/or b may be chosen so as to minimize correlation between $s_1$ and $n_1$ and/or between $s_2$ and $n_2$. One or more reference signals may then be generated from this signal model using any suitable technique. For example, a reference signal containing either one of $s_1$ (or $s_2$) and $n_1$ (or $n_2$) may be generated. A correlation canceller, such as an adaptive correlation canceller, may then be used to filter an input signal to remove those portions corresponding to signal portion contained in the reference signal.

In an embodiment, the reference signal may contain a noise portion, n, of an original signal, S. The reference signal may then be used to cancel the noise for an input signal using any suitable correlation cancellation technique. In the context of a PPG signal, the two signals, $S_1$ and $S_2$ of the above signal model may correspond to the red and infrared PPG signals. These signals may be filtered using the reference signal generated using the signal model as discussed above to remove noise in order to be able to derive physiological information, such as oxygen saturation information, pulse rate information, or any other suitable information from the PPG signals.

Alternatively, instead of relying on a signal model, a reference signal may be generated using continuous wavelet transforms as explained above. For example, the continuous wavelet transform may facilitate the identification and characterization of features within a signal. The regions and amplitudes within the scalogram associated with these features may then be isolated and extracted and used (possibly using the inverse wavelet transform) to produce a reference signal for future use. This new signal may be especially useful for the filtering or denoising of a signal (e.g., of a concurrently collected second signal).

For example, an artifact in the original signal may be identified in the scalogram through its abnormal shape and energy density with respect to its surroundings. Techniques for identifying artifacts in a scalogram are more fully discussed in commonly-assigned U.S. patent application Ser. No. 12/242, 861, entitled "SYSTEMS AND METHODS FOR ARTIFACT DETECTION IN SIGNALS" filed on Sep. 30, 2008, which is hereby incorporated by reference herein in its entirety. The amplitudes associated with this feature can then be extracted and an inverse CWT performed to produce a reference signal indicative of the artifact. The reference signal may then be used to filter or denoise a signal using conventional techniques, such as Kalman or LMS filtering.

Alternatively, the scalogram of extracted data may be used directly with the scalogram of the signal to be filtered to denoise the signal in the wavelet domain. This may have added advantages due to the filtering being applied in the time-scale space rather than the spectral or time domain.

Figure 9:
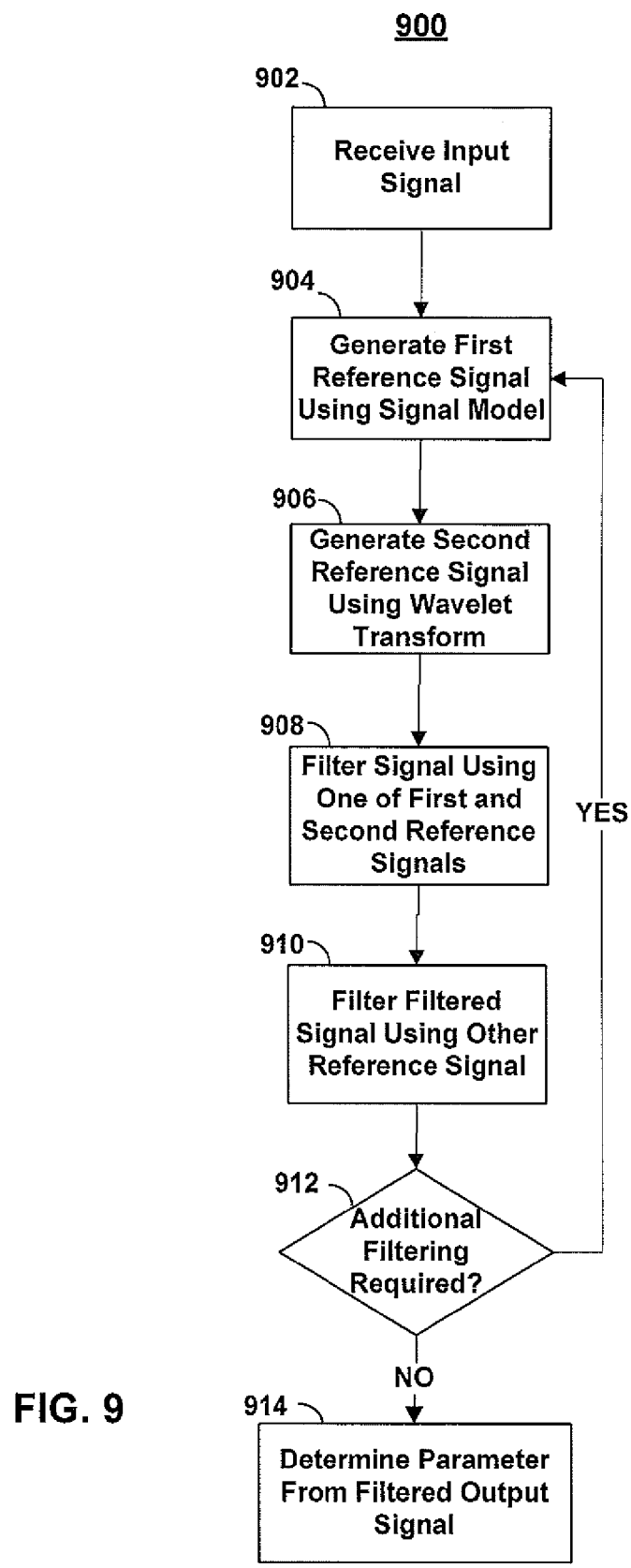
FIG. 9 shows an illustrative process for filtering a signal in accordance with an embodiment.

In one embodiment, a reference signal generated according to a signal model technique may be used together with another reference signal generated according to a wavelet transform technique as discussed above. For example, FIG. 9 shows illustrative process 900 for using both types of reference signals. At step 902, an input signal may be received. For example, a PPG signal may be received from sensor 12 (FIG. 2) or input signal generator 410 (FIG. 4). At step 904, a first reference signal may be generated according to a signal model. For example, microprocessor 48 (FIG. 2) or processor 412 (FIG. 4) may assume some mathematical relationship between two measured signals. A signal model may then be chosen so as to minimize the correlation between respective signal and noise components of one or both signals. At step 906, a second reference signal may be generated using a wavelet transform technique. For example, one or more of microprocessor 48 (FIG. 2), processor 412 (FIG. 4), wavelet transform calculator 502 (FIG. 5), and wavelet transform calculator 504 (FIG. 5) may generate the wavelet transform (or alternatively scalogram) of the input signal. It will be understood that the reference signals of steps 904 and 906 may be generated contemporaneously, or in any order. At step 908, the input signal may be filtered (e.g., using correlation cancellation) using one of the two reference signals to generate a filtered signal. At step 910, the filtered input signal may be filtered using the other reference signal. In the context of reference signals representing noise, this approach allows noise components identified by both the signal model technique and by the wavelet transform technique to be removed from an input signal.

At step 912, a determination may be made if additional filtering is required. If so, one or both of the filtering steps may be reapplied (using the same or different reference signals). If no additional filtering is required, then a parameter (e.g., a physiological parameter) may be determined at step 914 from the filtered output signal.

In practice, one or more steps shown in process 900 may be combined with other steps, performed in any suitable order, performed in parallel (e.g., simultaneously or substantially simultaneously), or removed.

Figure 10:
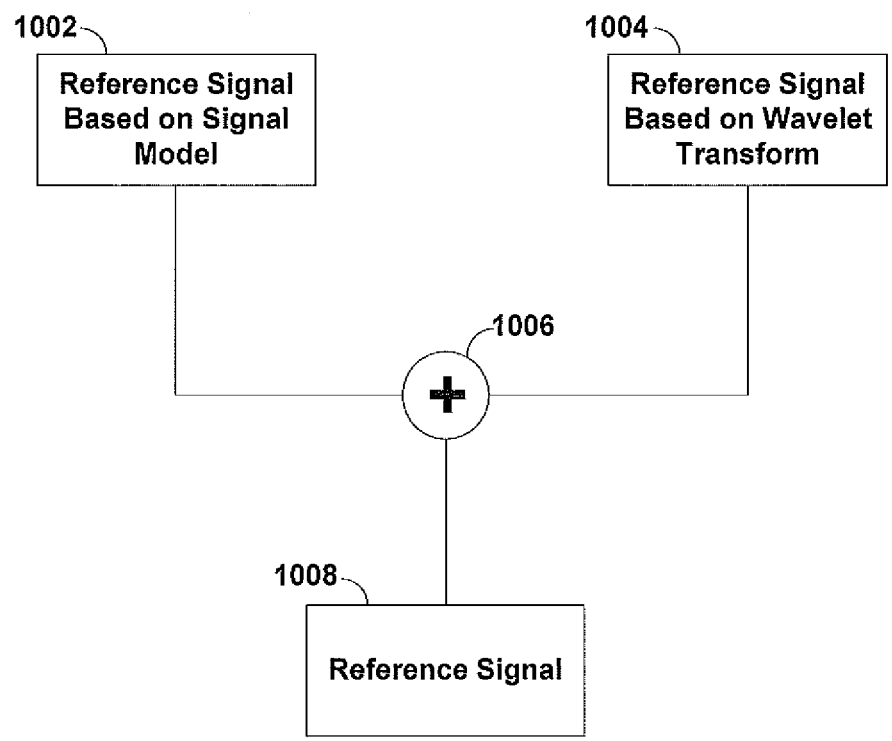
FIG. 10 shows an illustrative schematic of a system for generating a reference signal in accordance with an embodiment.

In one embodiment, a reference signal generated according to a signal model and a reference signal generated according to a wavelet transform may be combined to form a single reference signal. FIG. 10 shows a combined reference signal 1008 as being the sum of reference signal 1002, which was generated according to a signal model, and reference signal 1004, which was generated using a wavelet transform. Operator 1006, although shown to be addition, may be any other suitable operator for combining reference signals 1002 and 1004. Combined reference signal 1008 may then be used to filter an input signal, for example, using conventional adaptive filtering techniques.

With respect to PPG signals, cleaner red and infrared signals may be obtained by filtering them using at least the two reference signals discussed above with regard to FIGS. 9 and 10. More accurate and reliable physiological information may then be derived from the PPG signals.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

The invention claimed is:

1. A method for determining a physiological parameter, the method comprising:
   generating, using a pulse oximetry sensor, a first photoplethysmograph (PPG) signal corresponding to a first wavelength of light and a second PPG signal corresponding to a second wavelength of light;
   receiving, using a pulse oximeter, the first PPG signal and the second PPG signal;
   performing, using the pulse oximeter, a wavelet transform of the first PPG signal to generate a first set of complex transform numbers;
   generating, using the pulse oximeter, a first scalogram of real numbers based on a modulus operation performed on the first set of complex numbers;
   performing, using the pulse oximeter, a wavelet transform of the second PPG signal to generate a second set of complex transform numbers;
   generating, using the pulse oximeter, a second scalogram of real numbers based on a modulus operation performed on the second set of complex numbers;
   summing, using the pulse oximeter, the first scalogram and the second scalogram to generate a modified scalogram; and
   determining, using the pulse oximeter, the physiological parameter based on the modified scalogram.

2. The method of claim 1, wherein summing the first scalogram and the second scalogram comprises summing coefficients of the first scalogram and the second scalogram at each scale and time.

3. The method of claim 1, further comprising scaling, using the pulse oximeter, at least one of the first scalogram and the second scalogram before summing the first scalogram and the second scalogram.

4. The method of claim 3, wherein the scaling is based on noise.

5. The method of claim 3, wherein the scaling normalizes the first scalogram and the second scalogram.

6. The method of claim 1, wherein a characteristic of the wavelet transform of the first PPG signal is different than a characteristic of the wavelet transform of the second PPG signal.

7. The method of claim 1, wherein the physiological parameter is selected from the group comprising pulse rate and respiration rate.

8. A system for determining a physiological parameter, the system comprising:
   a pulse oximetry sensor configured to generate a first photoplethysmograph (PPG) signal corresponding to a first wavelength of light and a second PPG signal corresponding to a second wavelength of light; and
   a pulse oximeter coupled to the pulse oximetry sensor, wherein the pulse oximeter is configured to:
      receive the first PPG signal and the second PPG signal;
      perform a wavelet transform of the first PPG signal to generate a first set of complex transform numbers;
      generate a first scalogram of real numbers based on a modulus operation performed on the first set of complex numbers;
      perform a wavelet transform of the second PPG signal to generate a second set of complex transform numbers;
      generate a second scalogram of real numbers based on a modulus operation performed on the second set of complex numbers;
      sum the first scalogram and the second scalogram to generate a modified scalogram; and
      determine the physiological parameter based on the modified scalogram.

9. The system of claim 8, wherein the pulse oximeter is configured to sum coefficients of the first scalogram and the second scalogram at each scale and time.

10. The system of claim 8, wherein the pulse oximeter is further configured to scale at least one of the first scalogram and the second scalogram before summing the first scalogram and the second scalogram.

11. The system of claim 10, wherein the pulse oximeter is configured to scale based on noise.

12. The system of claim 10, wherein the pulse oximeter is configured to scale at least one of the first scalogram and the second scalogram to normalize the first scalogram and the second scalogram.

13. The system of claim 8, wherein a characteristic of the wavelet transform of the first PPG signal is different than a characteristic of the wavelet transform of the second PPG signal.

14. The system of claim 8, wherein the physiological parameter is selected from the group comprising pulse rate and respiration rate.

* * * * *